US008227582B2

(12) United States Patent
Ford et al.

(10) Patent No.: US 8,227,582 B2
(45) Date of Patent: Jul. 24, 2012

(54) PRODUCTION OF PLATINUM PARTICLE NUCLEIC ACID COMPOSITE COMPRISING SUBNANOMETER SIZE PARTICLES

(75) Inventors: William Ford, Stuttgart (DE); Jurina Wessels, Fellbach (DE); Oliver Harnack, Stuttgart (DE); Akio Yasuda, Stuttgart (DE)

(73) Assignee: Sony Deutschland GmbH, Cologne (DE)

(*) Notice: Subject to any disclaimer, the term of this patent is extended or adjusted under 35 U.S.C. 154(b) by 0 days.

(21) Appl. No.: 09/990,049

(22) Filed: Nov. 21, 2001

(65) Prior Publication Data

US 2002/0065242 A1 May 30, 2002

(30) Foreign Application Priority Data

Nov. 24, 2000 (EP) .................................... 00125823

(51) Int. Cl.
*C07H 19/00* (2006.01)
*C07H 21/00* (2006.01)
*C12N 15/11* (2006.01)

(52) U.S. Cl. ..................... 536/22.1; 514/44 R; 536/23.1

(58) Field of Classification Search ................. 536/22.1; 435/176; 514/44; 424/600
See application file for complete search history.

(56) References Cited

U.S. PATENT DOCUMENTS

| | | | | |
|---|---|---|---|---|
| 5,560,960 A | | 10/1996 | Singh et al. | 427/222 |
| 5,670,680 A | * | 9/1997 | Newman et al. | 556/53 |

FOREIGN PATENT DOCUMENTS

| | | |
|---|---|---|
| EP | 0 987 653 | 3/2000 |
| WO | WO 97 48837 | 12/1997 |
| WO | WO 99 04440 | 1/1999 |

OTHER PUBLICATIONS

Richter, Jan et al: "Nanoscale Palladium Metallization of DNA" XP000992850, pp. 507-510, 2000.

Pompe, Wolfgang et al: "Formation of Metallic Nanostructures on Biomolecular Templates" XP000992857, pp. 1085-1091, 1999.

Dressick et al., "Covalent Binding of Pd Catalysts to Ligating Self-Assembled Monolayer Films for Selective Electroless Metal Deposition"; J. Electrochem. Soc., vol. 141, No. 1, Jan. 1994; pp. 210-221.

* cited by examiner

*Primary Examiner* — David Naff

(74) *Attorney, Agent, or Firm* — Oblon, Spivak, McClelland, Maier & Neustadt, L.L.P.

(57) ABSTRACT

The present invention provides an improved process for the direct and selective metallization of nucleic acids via metal nanoparticles produced in-situ in which a nucleic acid specific metal complex is reacted with a nucleic acid to produce a metal complex-nucleic acid conjugate, non-conjugated metal complex and/or non-conjugated by-products are removed, and the metal complex-nucleic acid conjugate is reacted with a reducing agent to produce a metal nanoparticle-nucleic acid composite. The metal nanoparticle-nucleic acid composites may be used, e. g., in the formation of nanowires, for electronic networks and circuits allowing a high density arrangement.

14 Claims, 10 Drawing Sheets

MAJOR GROOVE SIDE

GUANINE CYTOSINE ADENINE THYMINE

MINOR GROOVE SIDE 1 leaving group 2 leaving groups (cis)

2 leaving groups (trans)

dinuclear

INTERCALATING AGENT
(Anthraquinone)

GROOVE BINDING AGENT
(Cationic porphyrin)

ALKYLATING AGENT
(Nitrogen mustard)

PRODUCTION OF PLATINUM PARTICLE NUCLEIC ACID COMPOSITE COMPRISING SUBNANOMETER SIZE PARTICLES

FIELD OF THE INVENTION

Background of the Invention

The present invention is related to an improved process for the direct and selective metallisation of nucleic acids via metal nanoparticles produced in-situ which can be used in the formation of nanowires, for electronic networks and circuits allowing a high density arrangement.

The electronic industry shows a constant effort in obtaining high density wiring and circuits. One key issue in reaching this goal is to make the individual wires as small as possible. One approach known in the prior art is the metallisation of nucleic acids which, once metallised, serves as an electrically conducting wire.

In addition, the "metalation" of nucleic acids is known, which refers to the process of direct bonding between a metal atom and a site within the nucleic acid, especially to the N-7 atoms of the purine nucleotides (G and A). Such reactions have been widely studied because of their relevance to the mechanisms of anti-cancer drugs, mostly Pt (II) or Pt (IV) complexes ("platination"). Other metal complexes exhibiting this behavior include the complexes of Pd, Ru, Au, Rh. The complex requires at least one "labile" ligand as a "leaving group" in order to bind in this manner.

Further, nucleic acid binding agents have been widely studied as anti-cancer drugs. Noncovalent binding agents include "intercalators" and "groove binders". Agents that bind covalently are generally called "alkylators". Many examples of each class of agents are known, as well as molecules with combined functions. Selectivity towards specific base pair combinations or sequences or other "recognition sites" is tuneable to a high degree (e.g. "drug targeting").

WO 99/04440, published on Jan. 28, 1999, describes a three-step process for the metallisation of DNA. First, silver ions ($Ag^+$) are localized along the DNA through $Ag^+/Na^+$ ion-exchange and formation of complexes between the $Ag^+$ and the DNA nucleotide bases. The silver ion/DNA complex is then reduced using a basic hydroquinone solution to form silver nanoparticles bound to the DNA skeleton. The silver nanoparticles are subsequently "developed" using an acidic solution of hydroquinone and $Ag^+$ under low light conditions, similar to the standard photographic procedure. This process produces silver wires with a width of about 100 nm with differential resistance of about 10M Ω.

However, a width of 100 nm and particularly a differential resistance of about 10M Ω of silver wires produced according to the process described in WO 99/04440 does not meet the need of industry in relation to high density wiring and high density circuits.

The metallisation procedure described in WO 99/04440 is similar to procedures for detecting fragments of DNA by silver staining. Such procedures are known to result in non-specific staining of the DNA fragments and do not distinguish between different DNA sequences. The ability to metallise certain regions of nucleic acid strand and not others may be critical for the development of DNA-based nanoelectronic devices.

Further, Pompe et al. (Pompe et al. (1999) *Z. Metallkd.* 90, 1085; Richter et al. (2000) *Adv. Mater.* 12, 507) describe DNA as a template for metallisation in order to produce metallic nanowires. Their metallisation method involves treating DNA with an aqueous solution of $Pd(CH_3COO)_2$ for 2 hours, then adding a solution of dimethylamine borane (DMAB) as reducing agent. Palladium nanoparticles with a diameter of 3-5 nm grow on the DNA within a few seconds of the reducing agent being added. After about 1 minute, quasi-continuous coverage is achieved, with metallic aggregates being 20 nm in size.

The techniques of nucleic acid synthesis and modification have been the subject of numerous publications. In particular, these methods are described in the books *Bioorganic Chemistry: Nucleic Acids* (edited by S. M. Hecht, Oxford University Press, 1996) and *Bioconiugate Techniques* (by G. T. Hermanson, Academic Press, 1996). More specifically, the chapter by M. Van Cleve in *Bioorganic Chemistry: Nucleic Acids* (Chapter 3, pages 75-104) describes the techniques of "annealing" and "ligation" for assembling double-stranded nucleic acids from smaller units. The chapter by M. J. O'Donnell and L. W. McLaughlin in the same book (Chapter 8, pages 216-243) and a chapter in *Bioconjugate Techniques* (Chapter 17, pages 639-671) describe procedures for chemical modification of nucleic acids and oligonucleotides and the covalent attachment of reporter groups (fluorophores, spin labels, etc.). These techniques have also been used to attach metal complexes to serve as, for example, redox-active agents and catalysts for bond cleavage, but they have not been used for metallisation purposes.

An example of chemical modification is "bromine activation". Reaction with N-bromosuccinimide, for example, causes bromination at the C-8 position of guanine residues and C-5 of cytosine (FIG. 7). Amine nucleophiles can then be coupled to these positions by nucleophilic displacement to introduce various functional groups into nucleic acids. The sites of derivation using this method are not involved in hydrogen bonding during base pairing, so hybridisation capabilities are not significantly disturbed.

The two prior art examples of DNA metallisation cited above as well as the present invention employ a principle present in both photographic film development and in electroless plating. These processes involve two steps: (1) formation of small metallic nanoparticles (or clusters) and (2) enlargement of the particles by electroless deposition of a metal, which may be the same or different from the first. The initially formed particles thus serve as nucleation sites for subsequent metal deposition.

"Two step" electroless plating processes are known from, for example, U.S. Pat. No. 5,503,877 and U.S. Pat. No. 5,560,960. The substrate to be plated is first exposed to a solution containing metal ion species and then to a solution of a reducing agent that reduces the metal ion species to a metal catalyst. The catalytic metal is usually Pd, but may be also at least one of Pd, Cu, Ag, Au, Ni, Pt, Ru, Rh, Os, and Ir, and is usually combined with an organic ligand containing at least one nitrogen atom. The deposited metal can be magnetic, e.g. Co, Ni, Fe and alloys, which may contain B or P introduced by the reducing agent (e.g. borohydride or hypophosphite, see U.S. Pat. No. 3,986,901; U.S. Pat. No. 4,177,253).

OBJECTS AND SUMMARY OF THE INVENTION

Accordingly, the problem underlying the present invention is to provide an improved process for the direct and selective metallisation of nucleic acids via metal nanoparticles produced in-situ which may be used, e. g., in the formation of nanowires, for electronic networks and circuits allowing a high density arrangement.

This problem is solved by the inventive process for producing metal nanoparticle-nucleic acid composites, in which a nucleic acid specific metal complex is reacted with a nucleic acid to produce a metal complex-nucleic acid conjugate, non-conjugated metal complex and/or non-conjugated by-products are removed, and the metal complex-nucleic acid conjugate is reacted with a reducing agent to produce a metal nanoparticle-nucleic acid composite.

The invention provides an improved method for the direct and selective metallisation of nucleic acids, e.g. DNA. After the addition of the reducing agent, no cluster formation can be observed on the DNA using AFM. This is in contrast to the method as described by Richter et al. in which irregular clusters are formed on the DNA which have a minimum size of about the same as the diameter of the DNA itself, indicating the uncontrolled growth of the metal particles on the DNA using this method. GoldEnhance® treatment of the DNA metallised according to the invention further shows, that the metallisation is mainly restricted to the DNA and therefore very intimate. Nevertheless, the metallised DNA can still be used for electroless metal deposition in order to produce nanowires or other nanocomponents.

Although the metallisation procedure described by Pompe et al. represents a significant advance over the one in WO 99/04440, the initially grown palladium nanoparticles are nonetheless substantially wider than DNA itself (ca. 2 nm for double-stranded DNA). The present invention describes a means of producing platinum nanoparticles on double-stranded DNA that are no wider than the DNA; these particles are catalytic towards electroless deposition of gold and can thereby be enlarged in a controlled manner. Also in contrast to the procedure of Pompe et al., the sub-nanometer size of the platinum particles in the nanoparticle/DNA composite produced according to the present invention are stable in time, at least for weeks or months. Thus, a single preparation of the composite can be utilised for, e.g., nanowire production at various times under various conditions. Furthermore, the present invention widens the possibilities for metallisation of pre-defined sites or segments within nucleic acids by providing several types of nanoparticle precursors and means of binding them to nucleic acids.

According to the invention, the nucleic acid component can be reacted dissolved in a solution, immobilised on a substrate or in a semisolid state, e.g. in a gel.

The nucleic acid for the metallisation can be selected from DNA, RNA, PNA, CNA, oligonucleotides, oligonucleotides of DNA, oligonucleotides of RNA, primers, A-DNA, B-DNA, Z-DNA, polynucleotides of DNA, polynucleotides of RNA, T-junctions of nucleic acids, triplexes and quadruplexes of nucleic acids, domains of non-nucleic acid polymer-nucleic acid blockcopolymers and combinations thereof. Suitable non-nucleic acid polymers for blockcopolymers can be polypeptides, polysaccharides, like dextrose or artificial polymers, like polyethyleneglycol (PEG) and are generally known to the person skilled in the art. The nucleic acids can be either double-stranded or single-stranded.

In a preferred process according to the invention, the metal complex-nucleic acid conjugate is formed by metalation and/or interactive ligand binding.

Even more preferred is a process according to the invention, which is characterised in that the nucleic acid specific metal complex is selected from the group comprising dichloro(2,2':6',2"-terpyridine)platinum(II), cis-diaminodichloroplatinum(II) and metal complexes with attached or integrated nucleic acid interacting groups, like intercalating, groove binding and alkylating agents.

In an even further preferred embodiment of the process according to the invention, the metal complex-nucleic acid conjugate is separated from non-conjugated metal complex and/or non-conjugated by-products by chromatography, like gel filtration or ion exchange, precipitation, like ethanol precipitation, or rinsing, for example with water or an aqueous salt solution.

In a further embodiment of the process according to the invention, the metal complex-nucleic acid conjugate is reacted with at least one reducing agent selected from the group comprising boron hydrides, borohydride salts, Lewis base:borane complexes of the general formula $L:BH_3$, in which L can be amine, ether, phosphine or sulfide, hydrazine and derivatives, hydroxylamine and derivatives, hypophosphite salts, formate salts, dithionite salts and $H_2$.

An even further preferred embodiment is characterised in that the reducing agent is used in the form of a gaseous reducing agent.

In general, the process according to the invention can be used for the selective metallisation of a nucleic acid. Preferred metal-nanoparticles are those who contain at least one metal selected from the group of Fe, Co, Ni, Cu, Ru, Rh, Pd, Ag, Os, Ir, Pt, Au or combinations (e.g. alloys) of these metals.

Preferred is a process which is characterised in that the metal nanoparticle is catalytically active towards electroless metallisation. More preferred is a process in which the metal nanoparticle can not be visualized by atomic force microscopy and/or that the diameter of the metal nanoparticle is smaller than 3 nm.

The problem underlying the invention is further solved by a process which further comprises the step of treating the metal nanoparticles within the metal nanoparticle-nucleic acid composite with an electroless plating solution in order to enlarge the metal nanoparticles.

In another embodiment, the metal complex-nucleic acid composite is treated dissolved in a solution, immobilized on a substrate or in a semisolid state, e.g. in a gel.

In a still further preferred embodiment of the process according to the invention the metal nanoparticles are treated with an electroless plating solution containing a mixture of the metals selected from the group comprising Fe, Co, Ni, Cu, Ru, Rh, Pd, Ag, Pt, Au or combinations (e.g. alloys) of these metals or magnetic and/or magnetized Fe, Co, Ni, or combinations (e.g. alloys) of these metals or combinations (e.g. alloys) of these metals with B or P.

The problem underlying the invention is further solved by a metal nanoparticle-nucleic acid composite which can be obtained according to on of the inventive methods.

Preferably, the metal nanoparticle-nucleic acid composite is characterized in that the diameter of the nanoparticles is smaller than 3 nm. More preferred is a metal nanoparticle-nucleic acid composite which is characterized in that that the nanoparticles can not be visualized by atomic force microscopy.

In an even further aspect of the invention, the problem is solved by a process for the manufacture of a nanowire, which is characterized by the following steps: a) providing a metal nanoparticle-nucleic acid composite according to the invention and b) growth, preferably controlled growth, of the nanoparticle by electroless deposition of a metal according to the invention.

In an even further aspect of the invention, the problem is solved by a linear array of metallic nanoparticles or a nanowire obtainable according to the inventive method. The metallic nanoparticles can be catalytic or magnetized. In a still further aspect the problem is solved by a nanowire which is obtainable by one of the inventive methods. The inventive nanowires can form an electronic network comprising at least one nanowire or an electronic circuit comprising at least one electronic network according to the invention. In addition, the inventive nanowires can be used as electronic components in their not completely metallised form, in which more or less insulating spaces are present between the individual nanoparticles positioned along the nucleic acid strand. In another aspect, the nanowires may be fully conducting or may contain insulating parts either at one or both ends, or the insulating parts may be within the wire itself, so that the nanowire is comprised of single conducting islands. These Inventive structures can form or can be part of an electronic network or an electronic circuit comprising at least one nanowire. In such electronic networks or electronic circuits, junctions between two or more wires may be formed, wherein each of the wires has a connecting segment proximal to the junction comprising the nanowire. Further, the nanowire comprising networks may be parts of hybrid electronic structures.

Further, the problem is solved by a junction between two or more wires of an electronic circuit, wherein each of the wires have an end segment proximal to the junction comprising a nanowire according to the invention.

BRIEF DESCRIPTION OF THE DRAWINGS

The invention will now be described in further detail with respect to the accompanying figures in which.

DETAILED DESCRIPTION OF THE INVENTION

Embodiments of the present invention essentially involve four steps:

Step (1): Binding of a metal complex to a nucleic acid to produce a metal complex-nucleic acid conjugate.

Figure 7:
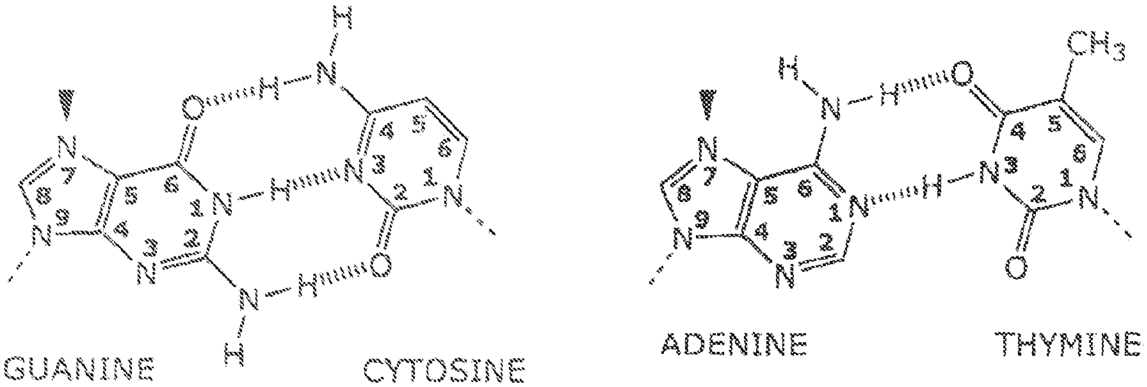
FIG. 7 shows the most likely positions for "metalation" at the N-7 atoms of the purine nucleotides (G and A) of a nucleic acid.

Specificity of the metalisation process for nucleic acids and for specific domains therein is determined primarily by the nature of binding in this step. The most straightforward binding approach is "metalation". This process refers to direct ("covalent") bonding between a metal atom and a site on the nucleic acid, especially the N-7 atoms of the purine nucleotides (G and A). These positions are indicated in FIG. 7. Such reactions have been widely studied because of their relevance to the mechanisms of anti-cancer drugs, mostly Pt (II) or Pt (IV) complexes ("platination"). The Pt (IV) complexes are generally considered to be "pro-drugs", since they are reduced in-vivo to the corresponding Pt (II) complexes before becoming active.

Figure 8:
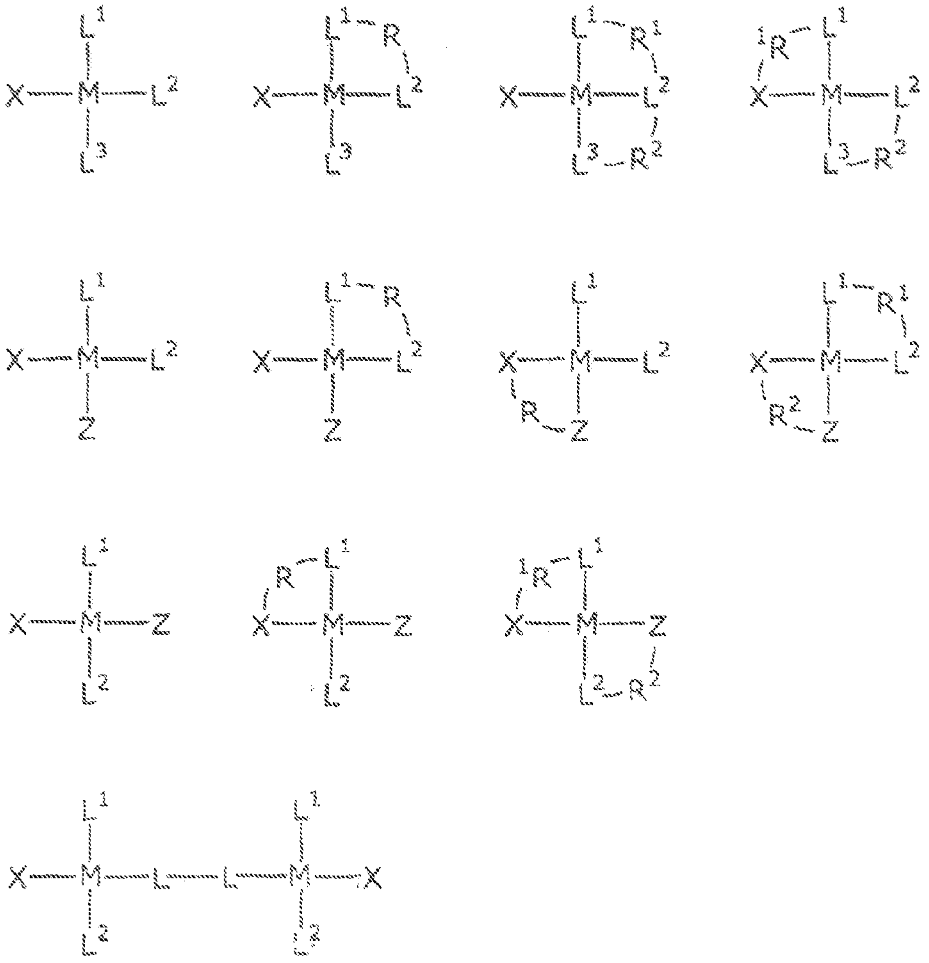
FIG. 8 shows several variations of metal (M)-ligand ($L^1$, $L^2$, and $L^3$, X or Z) complexes, (the charges have been omitted for simplicity).

Pt (II) complexes that are known to bind covalently to nucleic acids are generally square-planar, 4-coordinate species having the general formulae Pt($L^1$)($L^2$)(X)(Z) and Pt($L^1$)($L^2$)($L^3$)(X), where $L^1$, $L^2$, and $L^3$ represent ligands that are relatively inert towards replacement ("non-labile") and X and Z represent ligands that are relatively reactive towards replacement ("labile"). In these general formulae, the ligands $L^1$, $L^2$, and $L^3$ may be the same or different, and the ligands X and Z may be the same or different. Further, the ligands $L^1$, $L^2$, and $L^3$ may be connected by a bridging group to one another or to the ligands X or Z. Furthermore, the ligands X and Z may be "cis" or "trans" positions relative to one another with respect to the Pt(II) atom. Further still, the complex may contain two or more Pt(II) atoms. Some of these variations are indicated in FIG. 8.

The atoms in the non-labile ligands ($L^1$, $L^2$, and $L^3$) that are directly coordinated to Pt(II) are generally N, P, or S. Ligands that are not connected by bridging group(s) are called "monodentate". When two ligands are connected, they are called "bidentate", and when three are connected, they are "tridentate". Monodentate N-ligands are typically amines, monodentate P-ligands are typically phosphines, and monodentate S-ligands are typically thiols, thioethers or thiocarbonyls. The amine ligands can be ammonia, primary amines, secondary amines, or tertiary amines. These include aromatic amines such as pyridine and aniline. There are likewise many examples of bidentate N-N ligands in Pt(II) complexes known to bind covalently to nucleic acids. These include, for example, 1,2-diaminoethane, 1,2-diaminopropane, 1,3-diaminopropane, 1,2-diaminocylcohexane, and 2,2'-bipyridine. Examples of bidentate N-P and N-S ligands are also known, as well as tridentate N-N-N ligands such as 2,2':6',2"-terpyridine (terpy) and diethylenetriamine (dien).

Examples of the labile ligands X and Z that generally serve as good leaving groups include halide, water, (dialkyl)sulfoxides, nitrate, sulfate, carboxylates, dicarboxylates, carbonate, phosphate, pyrophosphate, phosphate esters, phosphonate, nitrite, sulfite, sulfonates, β-diketonates, alkenes, selenate, squarate, ascorbate and hydroxide. These ligands may be bidentate, as in the case of selenate and the dicarboxylates oxalate and 1,1-cyclobutanedicarboxylate, for example. They may also be part of a molecule containing non-labile ligand(s), as in amino acids (carboxylate and primary amine groups) and picolinic acid (carboxylate and pyridine groups), for example.

Complexes of other metals besides platinum have shown potential for use as anti-cancer drugs. These include complexes of Pd, Ru, Au, and Rh, which tend to be either 4-coordinate (e.g. square planar geometry) or 6-coordinate (e.g. octahedral geometry). As in the case of Pt(II) anti-cancer drugs, they also have at least one leaving group through which metalation of nucleic acid occurs. Due to stringent criteria for anti-cancer drugs, few of these other metal complexes have been clinically successful. If the complex is too labile, it is likely to interact with physiologic nucleophiles (proteins, etc.) before reaching its site of action in the tumor, thereby being deactivated or else increasing the risk of toxicity. On the other hand, if the complex is too inert, it may fail to interact with its biomolecular target as required to produce the anti-cancer effect. Complexes of Pd(II) are generally too labile, while those of Rh(III) are generally too inert; a problem with Au(III) complexes is the fact that they are easily reduced by physiological reducing agents. While these properties are problematic for application of the complexes as anti-cancer agents, they are much less so for application towards the metallisation of nucleic acids. Indeed, the enhanced reactivity of Pd(II) complexes compared to their Pt(II) analogues can be advantageous for this application, and extraneous reducing agents can be avoided in the case of Au(III) complexes.

Besides possessing at least one leaving group, the metalation complex should be capable of being reduced to a metallic state exhibiting catalytic activity towards electroless plating processes. Beyond Pt, these criteria are generally most likely to be fulfilled by complexes of Pd and Au. Complexes of Ru and Rh can also be used, however. The use of these metalation agents broadens the selectivity towards sequences or segments within nucleic acids as compared to the usual platination agents and also broadens the range of catalytic activity towards electroless plating.

Figure 9:
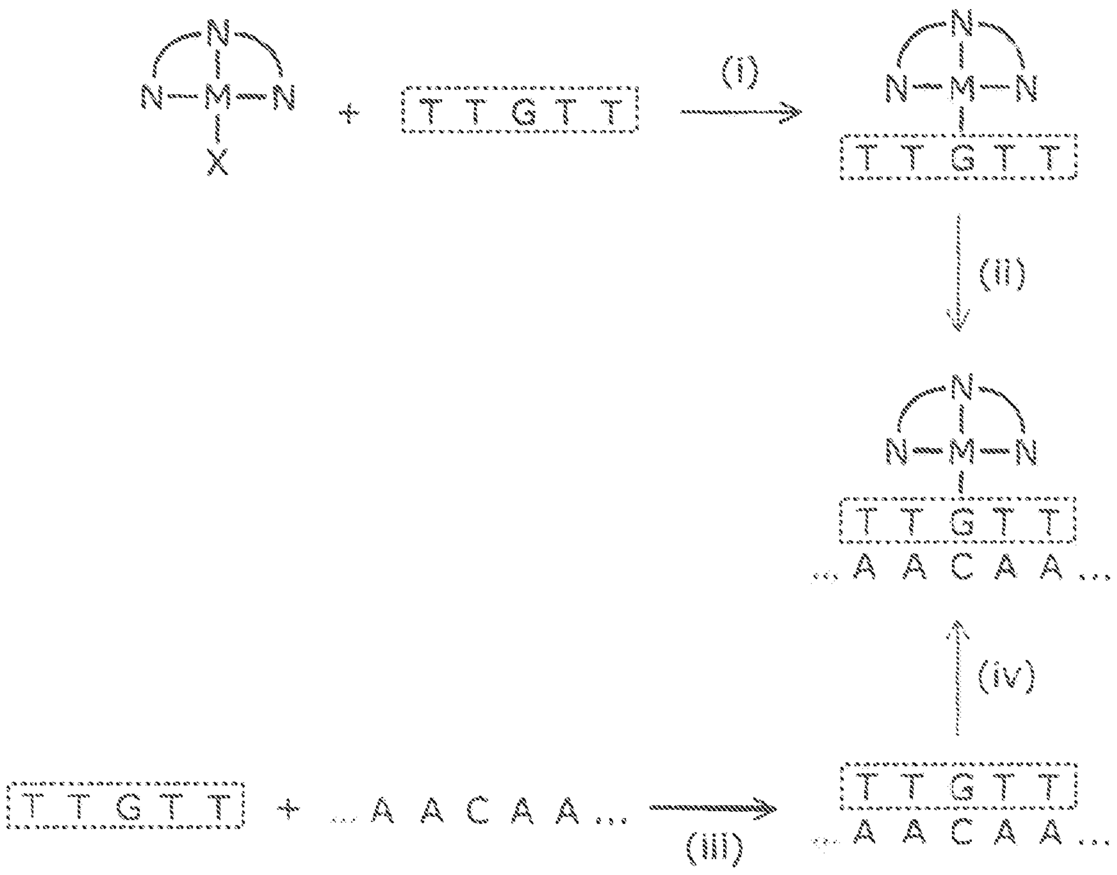
FIG. 9 schematically shows metalation of specific bases within oligonucleotide subunits at sites that are inherently present, (the charges have been omitted for simplicity)
Figure 10:
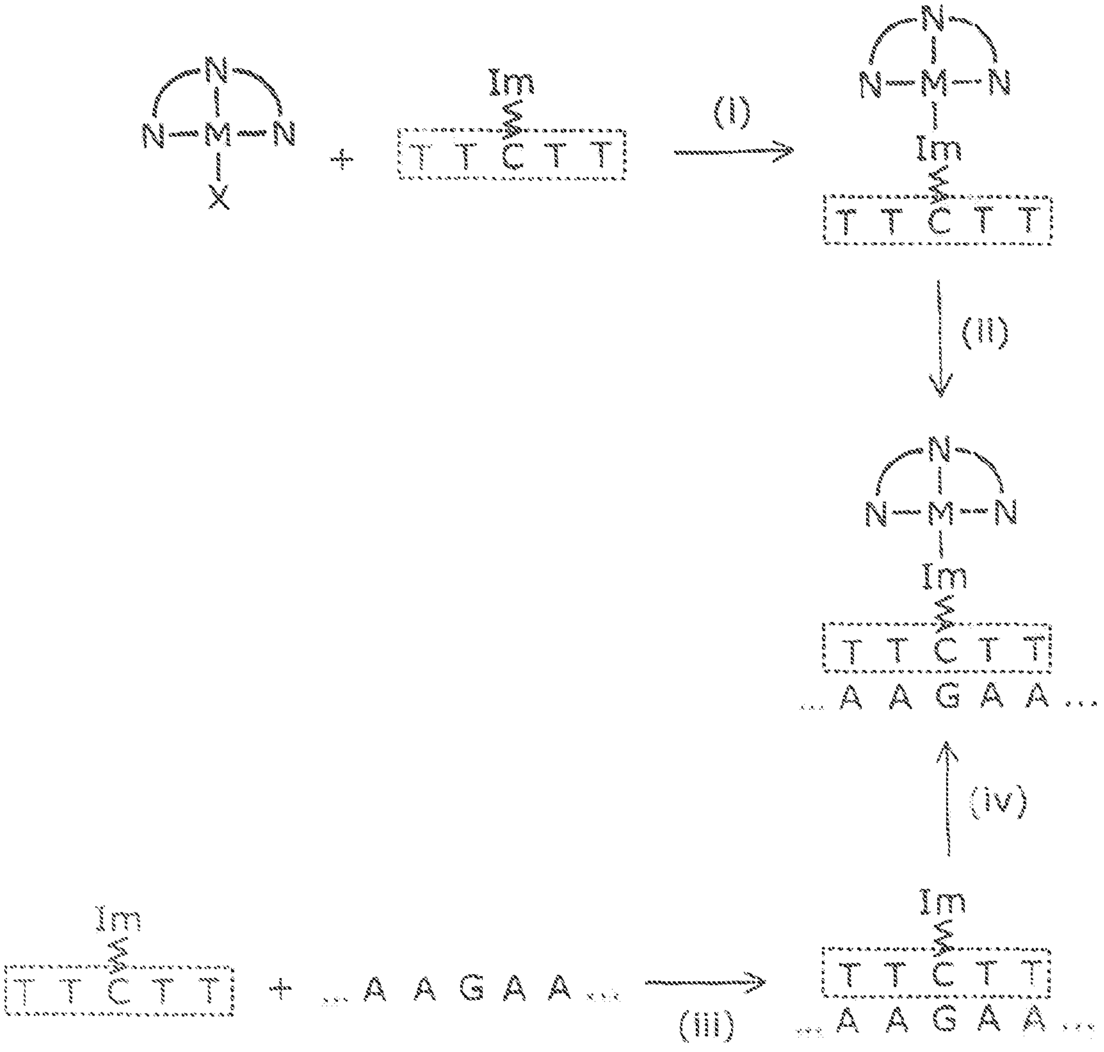
FIG. 10 schematically shows metalation of specific bases within oligonucleotide subunits at sites that have been introduced by chemical modification; (the charges have been omitted for simplicity).

In another embodiment of Step (1) of the invention, specific bases within oligonucleotide subunits are metalated. These subunits are assembled by hybridisation onto complementary segments of longer nucleic acids. Metalation of the targeted bases in the oligonucleotide subunits may be performed either before or after hybridisation. Non-complementary segments of the longer nucleic acid component are not hybridised by the metalated oligonucleotides; these gaps may be filled with other, complementary oligonucleotides that are not metalated, for example. Two variations of this embodiment are schematically illustrated in FIGS. 9 and 10. In one case (FIG. 9), metallisation occurs at a site that is inherently present in nucleic acids and in the other case (FIG. 10), metalation occurs at a site that has been introduced by chemical modification. Chemical modification of specific bases in the oligonucleotide subunits may be performed either before or after hybridisation.

In the example shown schematically in FIG. 9, a pentanucleotide having the sequence TTGTT is used as a subunit subject to metalation, and a metal complex having a tridentate (N-N-N) ligand and a leaving group (X) is used as metalating agent. Under mild conditions, (e.g. room temperature and neutral pH), the thymine (T) residue is essentially inert and only the guanine (G) residue is metalated: Two routes to the assembly of the metalated hybridised construct are indicated in the figure. In one process, the oligonucleotide is metalated (i) and then hybridised to the longer nucleic acid component (ii). In the other process, the oligonucleotide is hybridised first (iii) and then metalated (iv). This second process may require the use of modified bases in the longer nucleic acid component to prevent metalation of that component during step (iv). In a preferred embodiment, the oligonucleotide subunits are comprised of 4-20 bases and the metalation agents are complexes of Pt, Pd, Au, Ru, or Rh.

In the example shown schematically in FIG. 10, a pentanucleotide having the sequence TTC*TT is used as the subunit subject to metalation, where C* represents a cytosine residue that has been chemically modified to attach an imidazole (Im) group as a metal ligand. The imidazole group could be attached to the C-5 position of cytosine by bromine activation and nucleophilic displacement with 1-(3-aminopropyl)imidazole, for example. A metal complex having a tridentate (N-N-N) ligand and a leaving group (X) is used as metalating agent, as in the example in FIG. 9. As in that example, two routes to the assembly of the metalated hybridised construct are possible. In one process, the oligonucleotide is metalated (i) and then hybridised (ii). In the other process, the oligonucleotide is hybridised first (iii) an then metalated (iv). This second process may require the use of modified bases in the longer nucleic acid component to prevent metalation of that component during step (iv). In a preferred embodiment, the oligonucleotide subunits are comprised of 4-20 bases and the metalation agents are complexes of Pt, Pd, Au, Ru, or Rh.

In another embodiment of the invention, Step (1) is accomplished by a process in which ligands coordinated to the metal in the complex are not replaced upon binding. This type of binding can be classified as an "outer sphere" process. Counter-ion exchange whereby a metal ion (e.g. $Mg^{2+}$) is replaced by a similarly charged metal complex (e.g. $[Pt(NH_3)_4]^{2+}$) is an example, but such a simple exchange process provides little, if any, discrimination between nucleotide base sequences within the nucleic acid or between the nucleic acid and other negatively charged substances. Specificity for nucleic acids, and for specific domains therein, is achieved by attaching nucleic acid interactive groups to the metal complex. Such groups include intercalating, groove binding, and alkylating agents known from the prior art. The nucleic acid interactive group may be an integral part of a ligand coordinated to the metal ion (as in "metallointercalators") or else it may be covalently attached to a ligand. The main requirements of a metal complex used according to the invention are that it is relatively stable towards ligand exchange, so that the complex can be delivered to targeted nucleic acid binding sites intact. Further, it should be capable of being reduced to a metallic state exhibiting catalytic activity towards electroless plating processes. Both requirements are largely met by complexes of the metals of Groups 8 and 1B of the Periodic Table.

Compounds that are useful for this embodiment of Step (1) have the general structure $$\text{INT-CON-LIG-M(L)}_n$$

where INT is a nucleic acid interactive group, LIG is a non-labile ligand, and $M(L)_n$ is a coordinatively unsaturated metal-ligand complex which binds to LIG to complete the coordination requirements of the metal M. The group CON connects the INT and LIG groups and may function to spatially separate the INT and LIG groups and/or direct their relative orientations.

Metallointercalator complexes suitable for use according to this embodiment represent a special case of the general structure INT-CON-LIG-$M(L)_n$. Since the functions of INT and LIG are integrated, CON is not definable as a separate group. Suitable metallointercalators include complexes having the general formula $(ICL)M(L)_n$, where ICL is a planar aromatic ligand and M(L)n is a coordinatively unsaturated metal-ligand complex which binds to ICL to complete the coordination requirements of the metal M. Suitable metals M include Pt, Pd, and Au. Planar aromatic bidentate ligands whose metal complexes are known to interact with nucleic acids by intercalation include 8-hydroxyquinoline and α-diimines such as 2,2'-bipyridine, 1,10-phenanthroline, 2,2-biquinoline, dipyrido[3,2-a:2'3'-c]phenazine, and derivatives thereof. 2,2':6',2"-Terpyridine (terpy) is an example of a tridentate intercalator ligand. The function of the ligand(s) L in the group $M(L)_n$ is mainly to provide a relatively substitution-inert coordination environment for the metal, so a variety of non-labile monodentate or polydentate N-, P-, or S-ligands are possible. Suitable bidentate ligands include diamines such as 1,2-diaminoethane, 1,2-diaminopropane, 1,3-diaminopropane, and 1,2-diaminocyclohexane.

Figure 11:
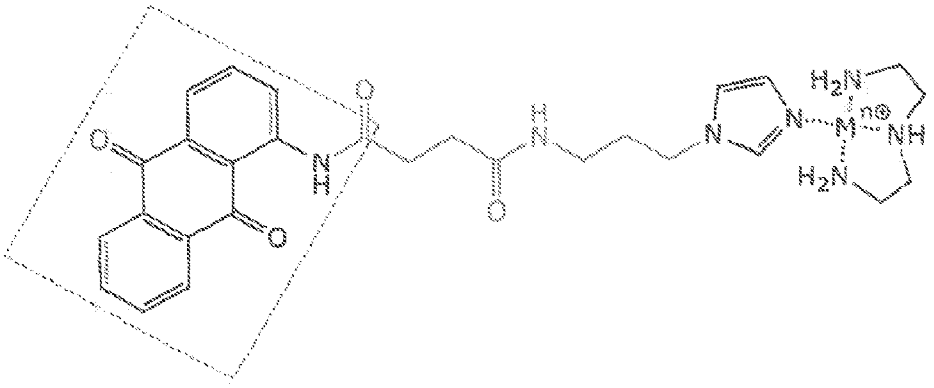
FIG. 11 shows examples of substitution-inert metal (M) complexes attached to nucleic acid interacting groups of the general formula INT-CON-LIG-M$(L)_n$.
Figure 11:
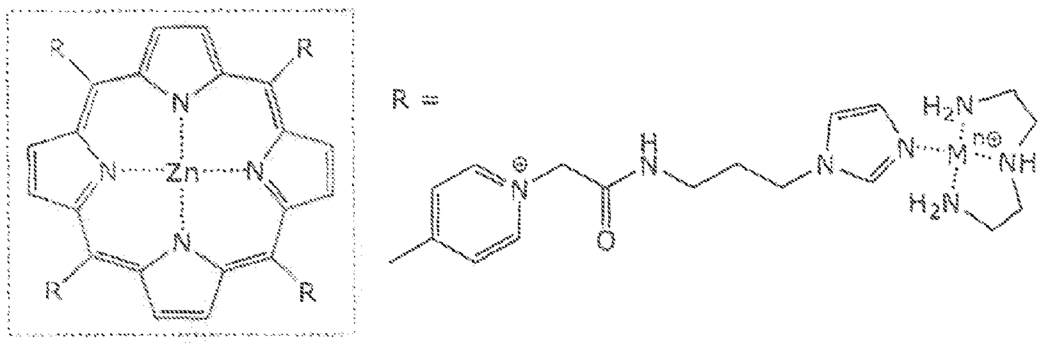
Figure 11:
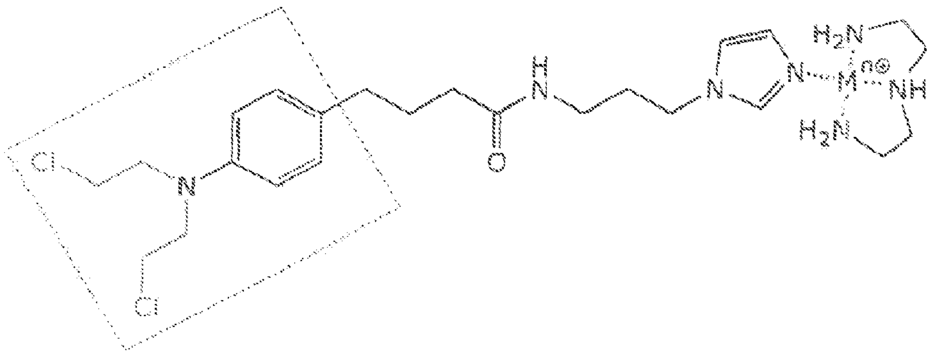

Specific examples of such compounds which incorporate complexes of Pt(II), Pd(II), or Au(III) are shown in FIG. 11. These compounds are prepared by covalently coupling the reagent 1-(3-aminopropyl)imidazole to a nucleic acid interacting group to produce examples of INT-CON-LIG, where the ligand is the N-3 atom of the appended imidazole group. The INT-CON-LIG compounds are then reacted with the metal complex of the form M(dien)(X), where dien is diethylenetriamine and X is a leaving group such as nitrate. The nucleic acid interacting groups in these examples consist of anthraquinone (an intercalating agent), a cationic porphyrin (a groove binding agent), and a nitrogen mustard (an alkylating agent).

In a further embodiment of Step (1) of the invention, substitution-inert metal complexes are covalently attached to specific bases within oligonucleotide subunits. These subunits are assembled by hybridisation onto complementary segments of longer nucleic acids. Covalent modification of the specific bases in the oligonucleotide may be performed either before or after hybridisation. Non-complementary segments of the longer nucleic acid component are not hybridised by the so-modified oligonucleotide; these gaps may be filled with other, complementary oligonucleotides to which metal complexes are not attached, for example. In the example shown schematically in FIG. 12, a pentanucleotide having the sequence TTG*TT is used as the subunit subject to metalation, where G* represents a guanine residue that has been chemically modified to attach an amine group (—$NH_2$) as a covalent bonding site. The amine group could be attached to the C-8 position of guanine by bromine activation and nucleophilic displacement with 1,4-diaminobutane, for example. The substitution-inert metal complex in this example has a tridentate (N-N-N) ligand and a monodentate amine ligand. The monodentate amine ligand is used for attaching a free carboxylic acid group (—COOH) to metal complex. Condensation of the carboxylic acid group on the metal complex with the amine group on the oligonucleotide subunit to form an amide bond —(—CONH—) provides linkage between those components. This condensation may be achieved using carbodiimide as a coupling reagent, for example.

Figure 12:
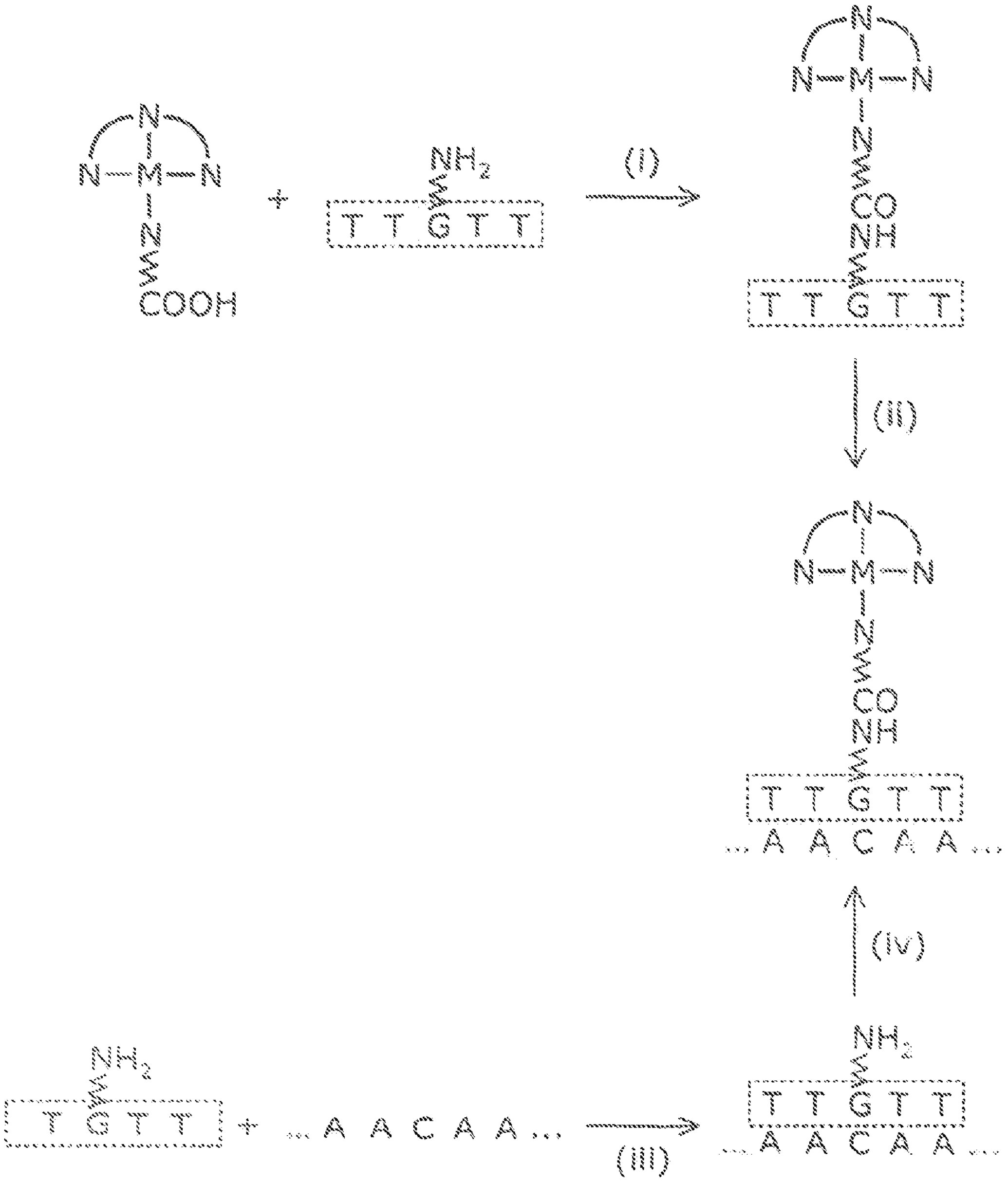
FIG. 12 schematically shows the covalent attachment of substitution-inert metal complexes to specific bases within oligonucleotide subunits, before or after hybridization at complementary segments of longer nucleic acids; (the charges have been omitted for simplicity).

Two possible routes to the assembly of the hybridised construct are indicated in FIG. 12. In one process, the oligonucleotide is coupled to the metal complex (i) and then hybridised to the longer nucleic acid component (ii). In the other process, the oligonucleotide is hybridised first (iii) and then coupled to the metal complex (iv). In a preferred embodiment, the oligonucleotide subunits are comprised of 4-20 bases and the metal complexes are complexes of Pt, Pd, Ru, Au or Rh.

Preferred embodiments for step (2) depend on whether metal complex-nucleic acid conjugate is dissolved in solution or immobilized on a substrate. When in solution, the conjugate can be separated from unbound metal complex by some form of chromatography (e.g., gel filtration or ion exchange) or by precipitation (e.g., ethanol precipitation of the conjugate). When the conjugate is immobilized, unbound metal complex can be removed by rinsing (e.g. with water or an aqueous salt solution).

Relatively strong reducing agents may be required for step (3). Suitable compounds are boron hydrides, particularly borohydride ($BH_4$) salts, Lewis base:borane complexes of the general formula $L:BH_3$, in which L can be amine, ether, phosphine or sulfide, hydrazine and derivatives, hydroxylamine and derivatives, hypophosphite salts, dithionite salts, formate salts and $H_2$. Some of these reagents are suitable as gaseous reducing agents for non-solution phase treatments.

Processes related to step (4) are known from prior art. Briefly, the metal nanoparticles in the composite act as catalytic sites for the reduction of metal ions in solution, which deposit onto and enlarge the nanoparticles. The deposited metal may be the same or different from that in the nanoparticle. The process can be used to enhance the electrical conductivity of the composite or to impart the particles with magnetic properties.

Figure 3:
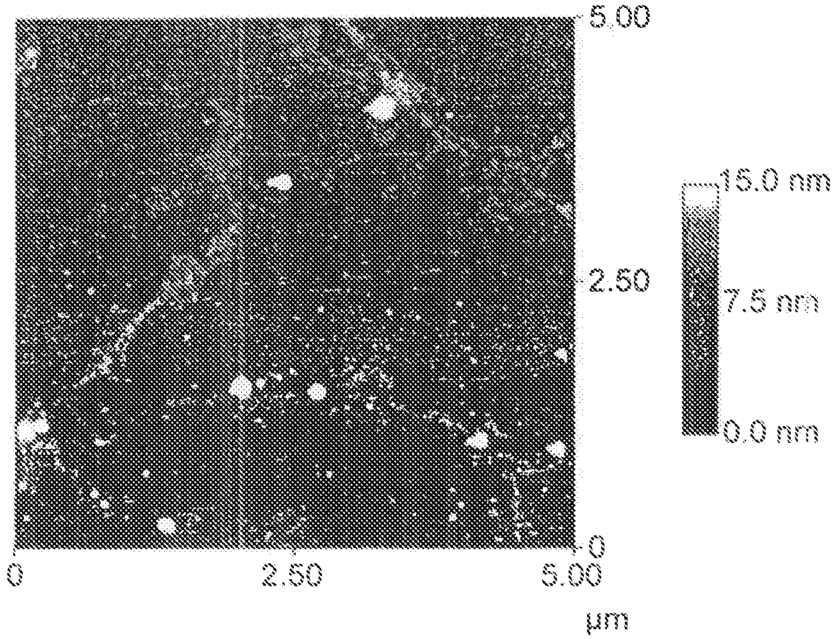
FIG. 3 shows an AFM image of a Pt-DNA composite produced according to Example 1 after treatment with a solution of GoldEnhance® according to Example 4.
Figure 4:
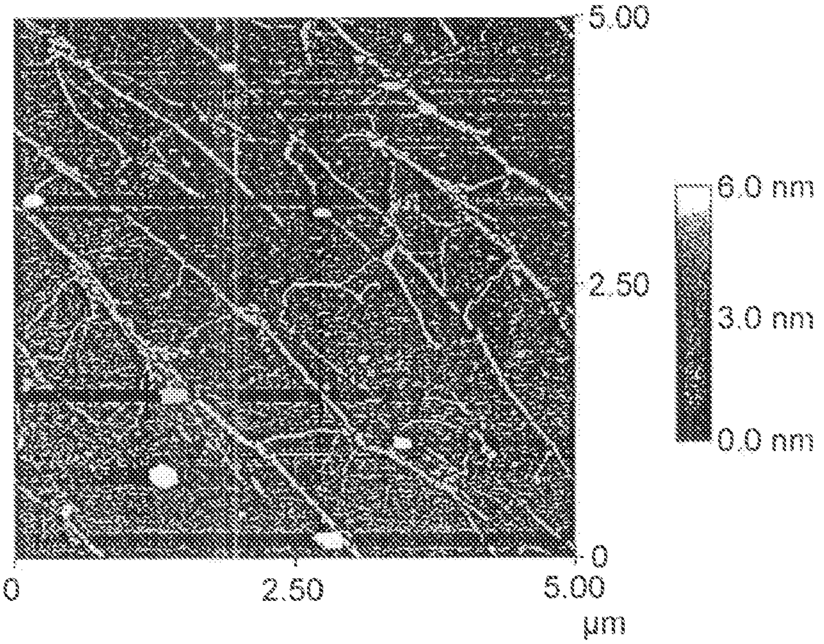
FIG. 4 shows an AFM image of another spot of the sample shown in FIG. 3.
Figure 6:
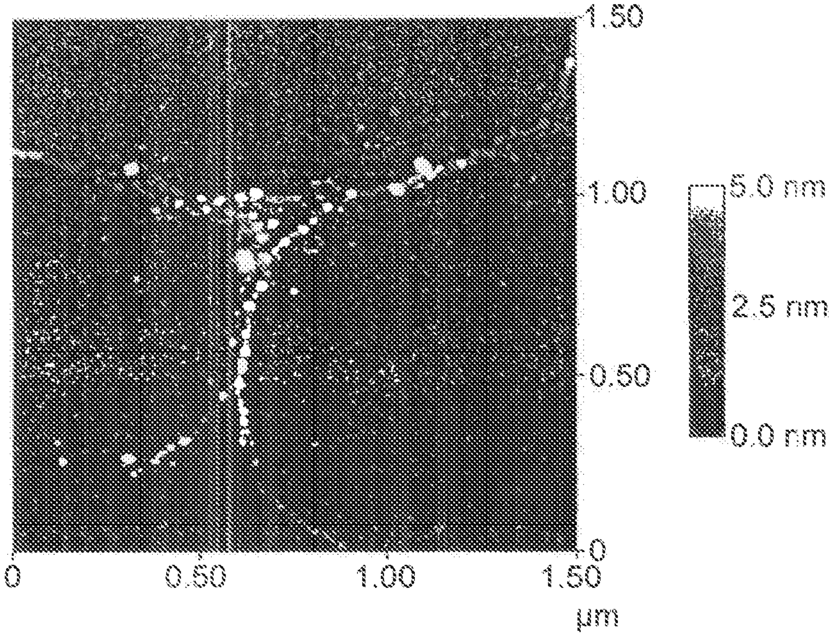
FIG. 6 shows an AFM image of a Pt-DNA composite produced according to Example 2 after treatment with a solution of GoldEnhance® according to Example 6.

Two pictures of Pt(terpy)-metallised DNA molecules are shown in FIGS. 3 and 4. FIG. 3 shows the presence of continuous metal coatings overlaying the elongated segments of DNA. The total thickness of these structures is between 3 nm and 6 nm in most places, but there are also islands where the thickness reaches ca 50 nm. FIG. 4 is an on the same sample showing discontinuous strings of metal particles along the elongated segments of DNA. Similar results have been obtained with cis-$Pt(NH_3)_2$-metallised DNA as shown in FIG. 6.

Nanoparticle-DNA Composites via Platinised Sodium Borohydride

Example 1

Figure 1:
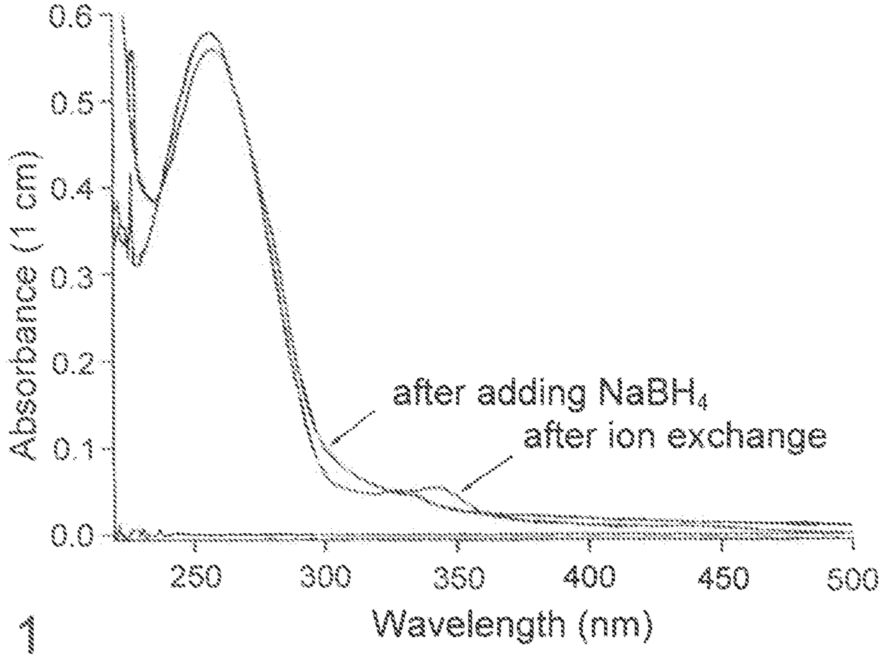
FIG. 1 shows the UV-visible absorption spectra of the Pt(II)-terpyridine-DNA conjugate and the Pt-DNA composites produced according to Example 1.

DNA (from calf thymus, Sigma-Aldrich product number D-1501) was dissolved in an aqueous solution containing 0.02M HEPES/NaOH buffer, pH 7.5. The equivalent concentration of nucleotide bases in the solution, estimated by UV-visible absorption spectroscopy, was 80 μM. To 2.5 mL of this solution was added 2.5 μL of a 0.020M solution of dichloro (2,2':6',2"-terpyridine)platinum(II) (Sigma-Aldrich product number 28, 809-8) in water. This complex is known to bind to DNA by a two-step process, a faster one involving intercalation of the terpyridine (terpy) ligand and a slower one involving covalent bond formation (platination) [Peyratout et al. (1995) *Inorg. Chem.* 34, 4484]. The resulting solution was kept in the dark at room temperature for 24 hours. It was then passed through a column of cation exchange gel (Sephadex-scope of protection C-25, Sigma-Aldrich product number 27, 131-4) using 0.02M HEPES/NaOH buffer as solvent to remove Pt-complexes that were not conjugated to the DNA. The UV-visible absorption spectrum of the solution after this treatment, presented in FIG. 1, shows distinct maxima near 340 nm, due to the terpy ligand coordinated to Pt, and 260 nm, due primarily to the DNA. By comparing the intensity of the absorption at 340 nm to the value measured before ion exchange, it was estimated that 30% of the initial amount of (terpy)Pt-complex was contained in the resulting (terpy)Pt-DNA conjugate.

Sodium borohydride (2 mg, Sigma-Aldrich product number 21, 346-2) was dissolved in 0.02M HEPES/NaOH buffer (100 μL), and 20 μL of that solution was added to 2.0 mL of the solution of (terpy)Pt-DNA conjugate. The colour of the solution changed immediately from pale yellow to pale grey, but the solution remained optically clear. The resultant change in the UV-visible absorption spectrum, obtained after 30 minutes, is consistent with the formation of colloidal Pt (FIG. 1). The pH of the solution was 7.8.

Example 2

Essentially the same procedure was used as in Example 1, except that 3.8 μL of a 0.013M solution of cis-diamminedichloroplatinum(II) ("cisplatin", Sigma-Aldrich product number P-4394) in 67% water-33% dimethylsufoxide was used instead, and only 2.5 hours was allowed before isolating the (diammine)Pt-DNA conjugate by cation exchange. Cisplatin is known to bind covalently to DNA, predominantly forming bifunctional intrastrand adducts between the N-7 atoms of adjacent G-G pairs or G-A pairs [Kelland (2000) *Drugs* 59 Suppl. 4, 1].

Atomic Force Microscopy Before and After Treatment With GoldEnhance®

Example 3

Figure 2:
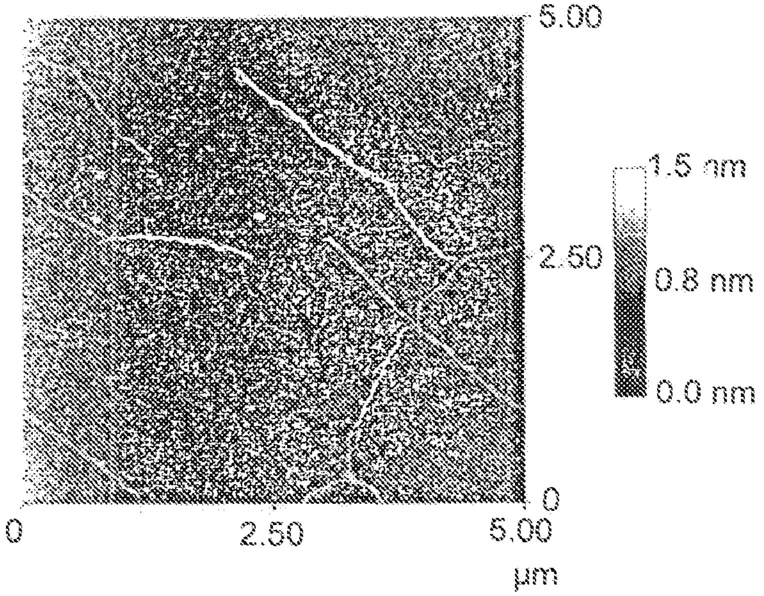
FIG. 2 shows an AFM image of a Pt-DNA composite produced according to Example 1 before treatment with a solution of GoldEnhance® according to Example 4.

The polished surface of a piece of silicon wafer (semiconductor grade, p-type, boron doped, with a native surface oxide) was treated with an $O_2$-plasma (Gala Instruments PlasmaPrep-5) for 4 minutes (0.4 mbar, at approx. 33 Watts, low power). The treated wafer was then mounted onto a spin-coater (Mikasa Spin-Coater 1H-D3). Several drops of the solution of Pt-DNA composite obtained in Example 1 were applied to the substrate. After 2 minutes, the sample was spun at 1000 rpm for 10 seconds, then immediately thereafter at 5000 rpm for 90 seconds. Two drops of water were dropped onto the sample during the second spin stage to remove salts. The sample was examined by tapping-mode AFM (Digital Instruments, MultiMode Atomic Force Microscope) using silicon nitride cantilevers (Olympus Optical, Micro Cantilever OMCL-AC160TS-W, approx. 250 kHz resonant frequency, approx. 25 N/m spring constant). The images (shown e.g. in FIG. 2) showed elongated segments of DNA without any evidence of Pt-particles.

Example 4

A solution of GoldEnhance® (Nanoprobes, catalogue number 2113) was applied to the surface of the substrate from Example 3 for 10 minutes, then the surface was rinsed with water and dried with a stream of air. Two AFM images of that sample are shown in FIGS. 3 and 4. FIG. 3 shows the presence of continuous metal coatings overlaying the elongated segments of DNA. The total thickness of these structures is between 3 nm and 6 nm in most places, but there are also islands where the thickness reaches ca 50 nm. FIG. 4 is an image of another spot on the same sample showing discontinuous strings of metal particles along the elongated segments of DNA. The total thickness of these structures is between 2 nm and 6 nm, but there are also islands where the thickness reaches ca 50 nm. It is also evident from the image that some segments of the DNA were not metallised. Both images show the surface of the silicon substrate relatively free of metal deposits, i.e., metallisation is mainly restricted to the DNA.

Example 5

Figure 5:
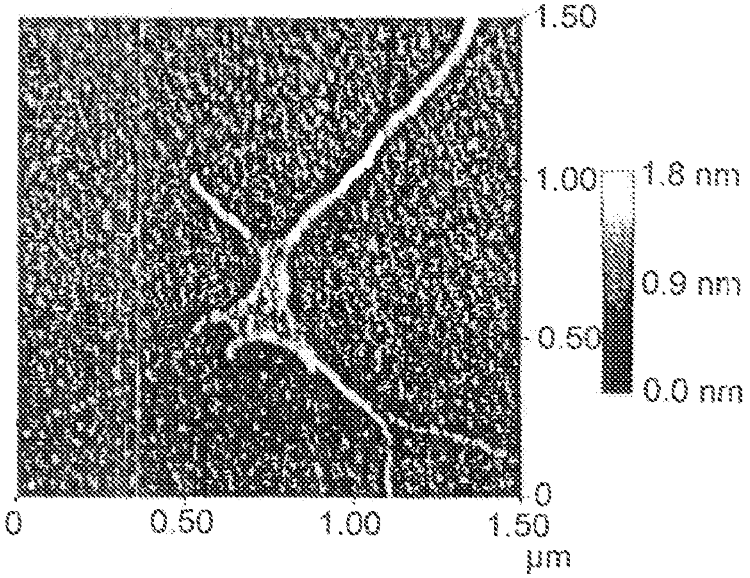
FIG. 5 shows an AFM image of a Pt-DNA composite produced according to Example 2 before treatment with a solution of GoldEnhance® according to Example 5.

A second silicon wafer was prepared as in Example 3 using the Pt-DNA composite solution from Example 2. AFM images (shown e.g. in FIG. 5) again showed elongated segments of DNA without any evidence of Pt-particles.

Example 6

The sample in Example 5 was treated with GoldEnhance® solution as described in Example 4. An AFM image obtained after this treatment is shown in FIG. 6. Similar to FIG. 4, this image shows discontinuous strings of metal particles along the elongated segments of DNA whose total thickness is between 2 nm and 6 nm, with non-metallised segments of thickness between 0.7 nm and 0.9 nm. The silicon wafer surface is essentially free of metal deposits.

Example 7

Figure 13:
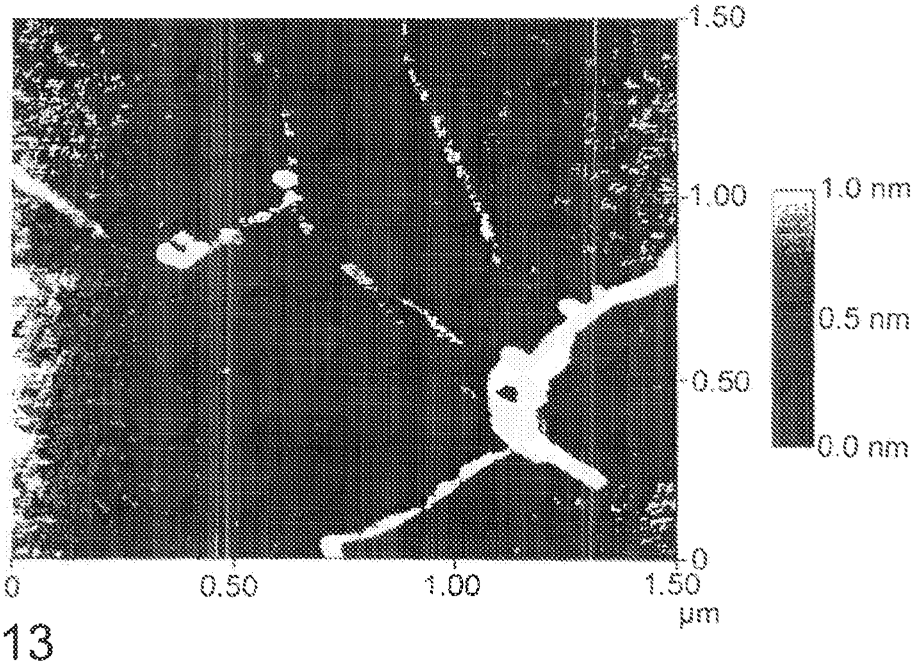
FIG. 13 shows an AFM image of an unmodified non-platinated DNA after treatment with a solution of GoldEnhance®.
Figure 14:
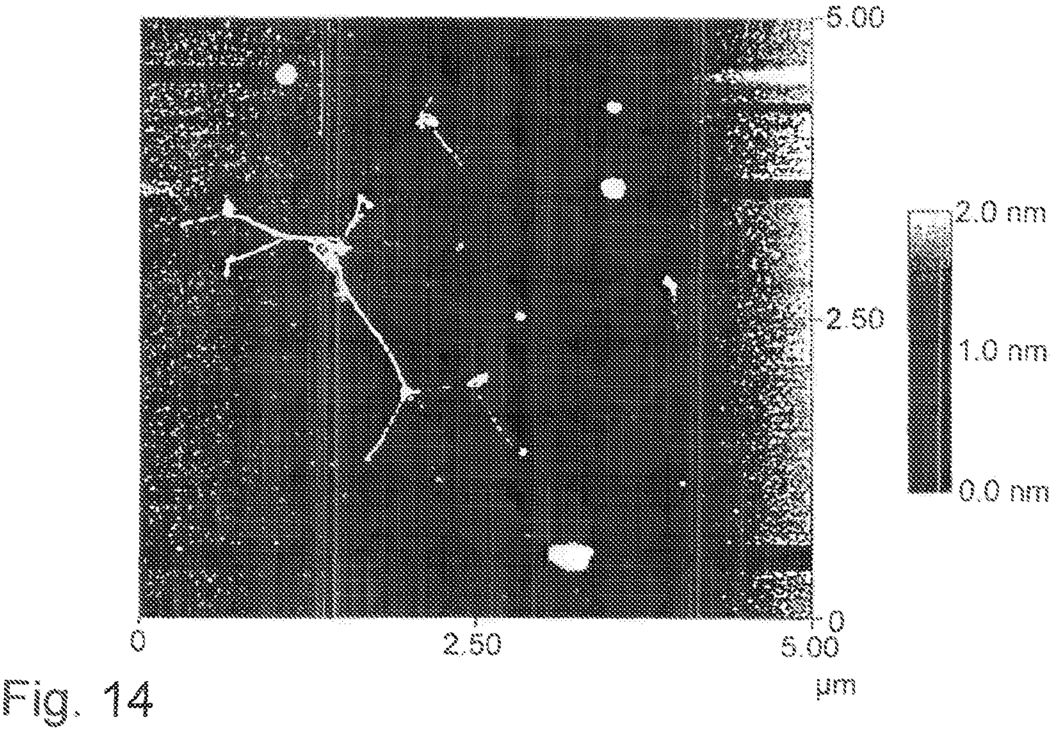
FIG. 14 shows an AFM image of an unmodified non-platinated DNA after treatment with a solution of GoldEnhance®.

Unmodified ct-DNA was immobilised and dried onto a silicon substrate as described in Example 3. It was then treated with GoldEnhance® solution for 15 minutes. AFM images as the ones in FIGS. 13 and 14 revealed some relatively large particles on the surface, but no particles were detectable on the DNA itself. This results show that platination is required for the DNA-localised particles seen in FIGS. 3, 4 and 6.

The invention claimed is:

1. A process for producing a platinum particle nucleic acid composite comprising platinum particles, the process comprising:

- providing a nucleic acid specific platinum complex selected from the group consisting of dichloro (2,2':6',2''-terpyridine)platinum (II), cis-diaminodichloroplatinum (II), and combinations thereof;
- reacting said nucleic acid specific platinum complex with a nucleic acid to produce a platinum complex-nucleic acid conjugate;
- removing any non-conjugated platinum complexes and/or non-conjugated by-products; and
- reacting the platinum complex-nucleic acid conjugate with a reducing agent to produce the platinum particle nucleic acid composite,
- wherein the platinum complex-nucleic acid conjugate is formed by the specific reacting of the nucleic acid specific platinum complex with bases of the nucleic acid,
- wherein the platinum particle nucleic acid composite is catalytically active towards electroless metallization,
- wherein the platinum particles in the platinum nucleic acid composite cannot be visualized by atomic force microscopy, and
- wherein the platinum particles in the platinum particle nucleic acid composite are subnanometer in size.

2. The process according to claim 1, wherein the nucleic acid is reacted while dissolved in solution, immobilized on a substrate or in a semisolid state with said nucleic acid specific complex.

3. The process according to claim 1, wherein the nucleic acid is selected from the group consisting of DNA, RNA, PNA, CNA, oligonucleotides, oligonucleotides of DNA, oligonucleotides of RNA, primers, A-DNA, B-DNA, Z-DNA, polynucleotides of DNA, polynucleotides of RNA, triplexes of nucleic acids quadruples of nucleic acids, and combinations thereof.

4. The process according to claim 1, wherein the nucleic acid is double-stranded or single-stranded.

5. The process according to claim 1, wherein the platinum complex-nucleic acid conjugate is removed from the non-conjugated platinum complexes and/or the non-conjugated by-products by chromatography, precipitation or rinsing.

6. The process according to claim 1, wherein the platinum complex-nucleic acid conjugate is reacted with at least one reducing agent selected from the group consisting of a boron hydride, a borohydride salt, a Lewis base: borane complex of formula L:$BH_3$, wherein L is an amine, an ether, a phosphine, a sulfide, a hydrazine, a hydroxylamine, a hypophosphite salt, formate salt, a dithionite salt, and $H_2$.

7. The process according to claim 6, wherein the reducing agent is a gaseous reducing agent.

8. The process according to claim 1, further comprising treating the platinum particles within the platinum particle nucleic acid composite with an elecroless plating solution to enlarge the platinum particles.

9. The process according to claim 8, wherein the platinum particles within the platinum complex-nucleic acid conjugate are treated while dissolved in solution, immobilized on a substrate or in a semisolid state with an electroless plating solution.

10. The process according to claim 8, wherein the platinum particles within the platinum particle nucleic acid composite are treated with an electroless plating solution comprising at least one metal selected from the group consisting of Fe, Co, Ni, Cu, Ru, Rh, Pd, Os, Ir Ag, Pt, Au and combinations thereof.

11. The process according to claim 8, wherein the platinum particles of the composite are treated with an electroless plating solution comprising at least one material selected from the group consisting of magnetic Fe, Co, Ni, a combination of these metals, and a combination of these metals with boron (B) or phosphorus (P).

12. The process according to claim 2, wherein the nucleic acid is reacted in a semisolid state, and wherein the semisolid state is a gel.

13. The process according to claim 5, wherein the metal complex-nucleic acid conjugate is removed from the non-conjugated metal complex and/or the non-conjugated by-products by gel filtration chromatography, ion exchange chromatography, ethanol precipitation, water rinsing or aqueous salt solution rinsing.

14. A platinum particle nucleic acid composite produced by the method of claim 1.

* * * * *